(12) United States Patent
Chuang et al.

(10) Patent No.: US 10,722,620 B2
(45) Date of Patent: *Jul. 28, 2020

(54) SURGICAL IRRIGATION AND SUCTION CONTROL APPARATUS AND CONTROL METHOD THEREOF

(71) Applicant: INTAI TECHNOLOGY CORP., Taichung (TW)

(72) Inventors: Shih-Chang Chuang, Taichung (TW); Dian-Ying Lin, Taichung (TW)

(73) Assignee: INTAI TECHNOLOGY CORP., Taichung (TW)

( * ) Notice: Subject to any disclaimer, the term of this patent is extended or adjusted under 35 U.S.C. 154(b) by 97 days.

This patent is subject to a terminal disclaimer.

(21) Appl. No.: 15/472,256

(22) Filed: Mar. 28, 2017

(65) Prior Publication Data

US 2018/0161483 A1 Jun. 14, 2018

Related U.S. Application Data

(63) Continuation-in-part of application No. 15/376,628, filed on Dec. 12, 2016, now abandoned.

(51) Int. Cl.
  *A61M 1/00* (2006.01)
  *A61M 3/02* (2006.01)
  *A61B 1/015* (2006.01)

(52) U.S. Cl.
  CPC ........... *A61M 1/0058* (2013.01); *A61B 1/015* (2013.01); *A61M 1/0045* (2014.02);
  (Continued)

(58) Field of Classification Search
  CPC .............. A61M 1/0058; A61M 1/0062; A61M 1/0064; A61M 3/0279; A61M 3/0283;
  (Continued)

(56) References Cited

U.S. PATENT DOCUMENTS 5,078,681 A * 1/1992 Kawashima ....... A61B 1/00082
  604/103.11
5,195,959 A * 3/1993 Smith ................ A61B 18/1402
  604/34

(Continued)

FOREIGN PATENT DOCUMENTS

| CN | 201244015 Y | 5/2009 |
| CN | 203989395 U | 12/2014 |
| TW | M306863 U | 3/2007 |

*Primary Examiner* — Bhisma Mehta
*Assistant Examiner* — Hong-Van N Trinh
(74) *Attorney, Agent, or Firm* — CKC & Partners Co., LLC

(57) ABSTRACT

A surgical irrigation and suction control apparatus connecting to an irrigation device and a suction device includes a flexible cannula, a grip, a first tube, a second tube, an irrigation control unit and a suction control unit. The grip is connected to the flexible cannula. The irrigation control unit includes an irrigation switch and an irrigation tube. The irrigation tube is flexible and is connected between the second tube and the irrigation device. The irrigation switch is disposed on the grip and is actuated to change a diameter of the irrigation tube. The suction control unit includes a suction switch and a suction tube. The suction tube is flexible and is connected between the second tube and the suction device. The suction switch is disposed on the grip and is actuated to change a diameter of the suction tube.

11 Claims, 21 Drawing Sheets

(52) U.S. Cl.
CPC ........ *A61M 1/0064* (2013.01); *A61M 3/0283* (2013.01); *A61M 3/0279* (2013.01)

(58) Field of Classification Search
CPC .............. A61M 1/0045; A61M 1/0084; A61M 1/0043; A61M 1/0039; A61M 1/0041; A61B 1/015; A61B 2218/001
See application file for complete search history.

(56) References Cited

U.S. PATENT DOCUMENTS

| | | | | |
|---|---|---|---|---|
| 5,250,065 | A | * | 10/1993 | Clement ........ A61B 17/320016 600/571 |
| 5,254,117 | A | * | 10/1993 | Rigby ................ A61B 18/1482 606/42 |
| 5,312,373 | A | * | 5/1994 | Freitas ................ A61M 1/0064 604/249 |
| 5,354,291 | A | * | 10/1994 | Bales ................ A61M 1/0064 604/22 |
| 5,609,573 | A | * | 3/1997 | Sandock ............ A61B 18/1482 604/22 |
| 5,613,954 | A | | 3/1997 | Nelson et al. |
| 6,149,622 | A | * | 11/2000 | Marie ................ A61M 1/0043 604/119 |
| 6,179,807 | B1 | | 1/2001 | Henniges et al. |
| 6,364,853 | B1 | * | 4/2002 | French ................ A61M 1/0064 137/596.2 |
| 2007/0005002 | A1 | | 1/2007 | Millman et al. |
| 2014/0207056 | A1 | * | 7/2014 | Bono ................ A61M 1/0064 604/34 |

* cited by examiner

SURGICAL IRRIGATION AND SUCTION CONTROL APPARATUS AND CONTROL METHOD THEREOF

RELATED APPLICATIONS

This application a Continuation-in-part of U.S. application Ser. No. 15/376,628, filed on Dec. 12, 2016, the entirety of whit h is incorporated by reference herein.

BACKGROUND

Technical Field

The present disclosure relates to an irrigation and suction control apparatus and an irrigation and suction control method. More particularly, the present disclosure relates to a surgical irrigation and suction control apparatus and a surgical irrigation and suction control method.

Description of Related Art

During medical procedures, it is common to irrigate or wash a wound with sterilized fluid, such as physiological saline. Furthermore, during surgical procedures, the physician or other health professionals may utilize the irrigation fluid for hydrodissection. In both procedures, the irrigation fluid is provided from a source or a reservoir of fluid of an irrigation device. Commonly, the irrigation fluid is provided under pressure to the surgical site. Furthermore, the physicians and other health professionals also utilize suction to remove spent irrigation fluid, at her bodily fluids and debris which may accumulate at the wound site or surgical site. In certain medical procedures, the physician utilizes suction to remove gas. Gas will sometimes hurt the brain tissue at a brain surgical site. Suction, or negative air pressure (some pressure below the ambient pressure), is created by a suction device.

Various kinds of irrigation and suction control apparatuses have been developed in the market. However, they have complex structure and high, manufacturing cost. Therefore, it is commercially desirable to develop an irrigation and suction control apparatus and a control method thereof that are easy to use, have low manufacturing cost and can be easily operated by the hand of an operator or a physician.

SUMMARY

According to one aspect of the present disclosure, a surgical irrigation and suction control apparatus connecting to an irrigation device and a suction device includes a flexible cannula, a grip, a first tube, a second tube, an irrigation control unit and a suction control unit. The flexible cannula includes an inner space. The grip is connected to the flexible cannula and includes an accommodating space communicated with the inner space. The first tube is through the inner space and the accommodating space. The second tube includes a connecting portion. The second tube is through the inner space, and the connecting portion of the second tube is located in the accommodating space. The irrigation control unit includes an irrigation switch and an irrigation tube. The irrigation tube is flexible and is connected between the connecting portion of the second tube and the irrigation device. The irrigation, switch is disposed on the grip, and the irrigation switch is actuated to change a diameter of the irrigation tube. The suction control unit includes a suction switch and a suction tube. The suction tube is flexible and is connected between the connecting portion of the second tube and the suction device. The suction switch is disposed on the grip, and the suction switch is to change a diameter of the irrigation to be. An inner diameter of the second tube is equal to or smaller than an inner diameter of the irrigation tube and an inner diameter of the suction tube.

According to another aspect of the present disclosure, a surgical irrigation and suction control apparatus connecting to an irrigation device and a suction device includes a flexible cannula, a grip, a first tube, a second tube, an irrigation control unit, a suction control unit and a partitioning member. The flexible cannula includes an inner space. The grip is connected to the flexible cannula and includes an accommodating space communicated with the inner space. The first tube is through the inner space and the accommodating space. The second tube includes a connecting portion. The second tube is through the inner space, and the connecting portion of the second tube is located in the accommodating space. The irrigation control unit includes an irrigation switch and an irrigation tube. The irrigation tube 620 is flexible. One end of the irrigation tube is connected to the irrigation device. The irrigation switch is disposed on the grip. The irrigation switch is actuated to change a diameter of the irrigation tube. The suction control unit includes a suction switch and a suction tube. The suction tube is flexible, and one end of the suction tube is connected to the suction device. The suction switch is disposed on the grip, and the suction switch is actuated to change a diameter of the irrigation tube. The partitioning member has three terminals which are connected to the connecting portion, the other end of the irrigation tube and the other end of the suction tube, respectively. An outer diameter of the second tube is equal to an inner diameter of the terminal which is connected to the connecting portion. An inner diameter of the other end of the irrigation tube is equal to an outer diameter of the terminal which is connected to the other end of the irrigation tube, and an inner diameter of the other end of the suction tube is equal to an outer diameter of the terminal which is connected to the other end of the suction tube.

According to further another aspect of the present disclosure, a surgical irrigation and suction control method for operating a surgical irrigation and suction control apparatus includes an irrigating step and a sucking step. The irrigating step is for pressing an irrigation switch to increase a diameter of an irrigation tube so as to communicate an irrigation device with a second tube via the irrigation tube. The sucking step is for pressing a suction switch to increase a diameter of a suction tube so as to communicate a suction device with the second tube via the suction to be. The irrigating step and the sucking step are operated simultaneously.

BRIEF DESCRIPTION OF THE DRAWINGS

The present disclosure can be more fully understood by reading the following detailed description of the embodiment, with reference made to the accompanying drawings as follows.

DETAILED DESCRIPTION

Figure 1:
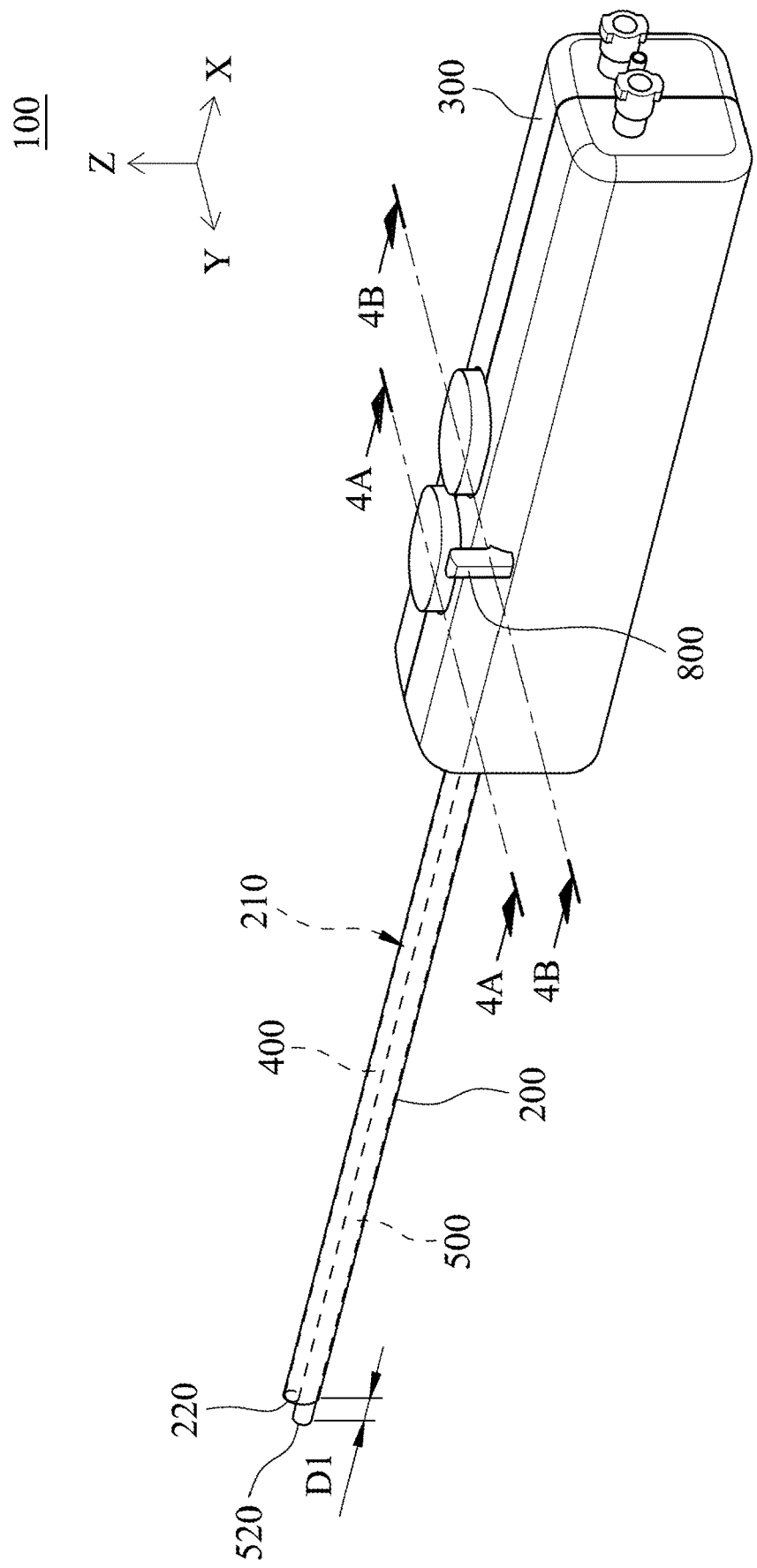
FIG. 1 is a schematic view showing a surgical irrigation and suction control apparatus according to one embodiment of the present disclosure.
Figure 2:
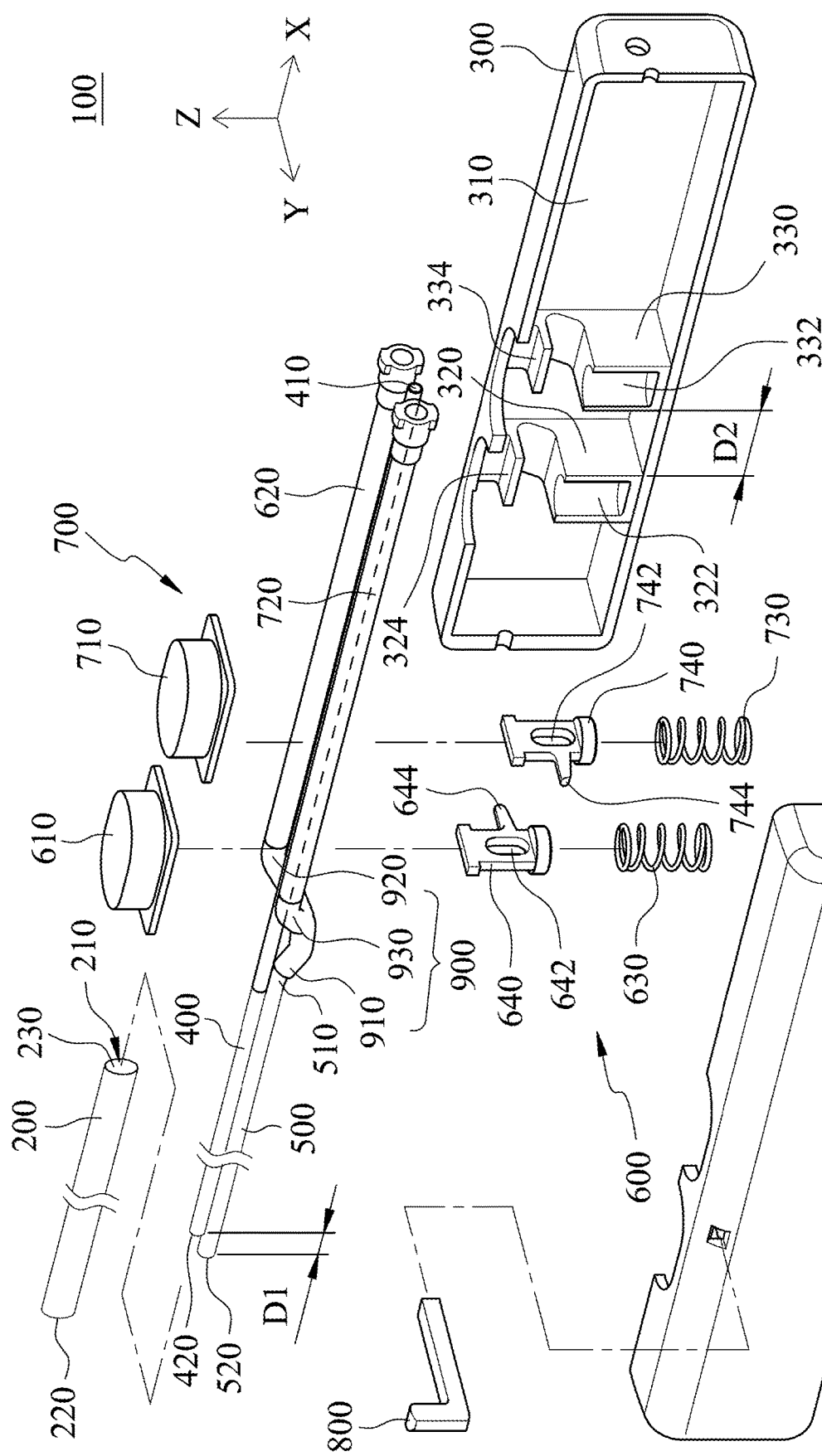
FIG. 2 is an exploded view showing the surgical irrigation and suction control apparatus of FIG. 1.
Figure 3:
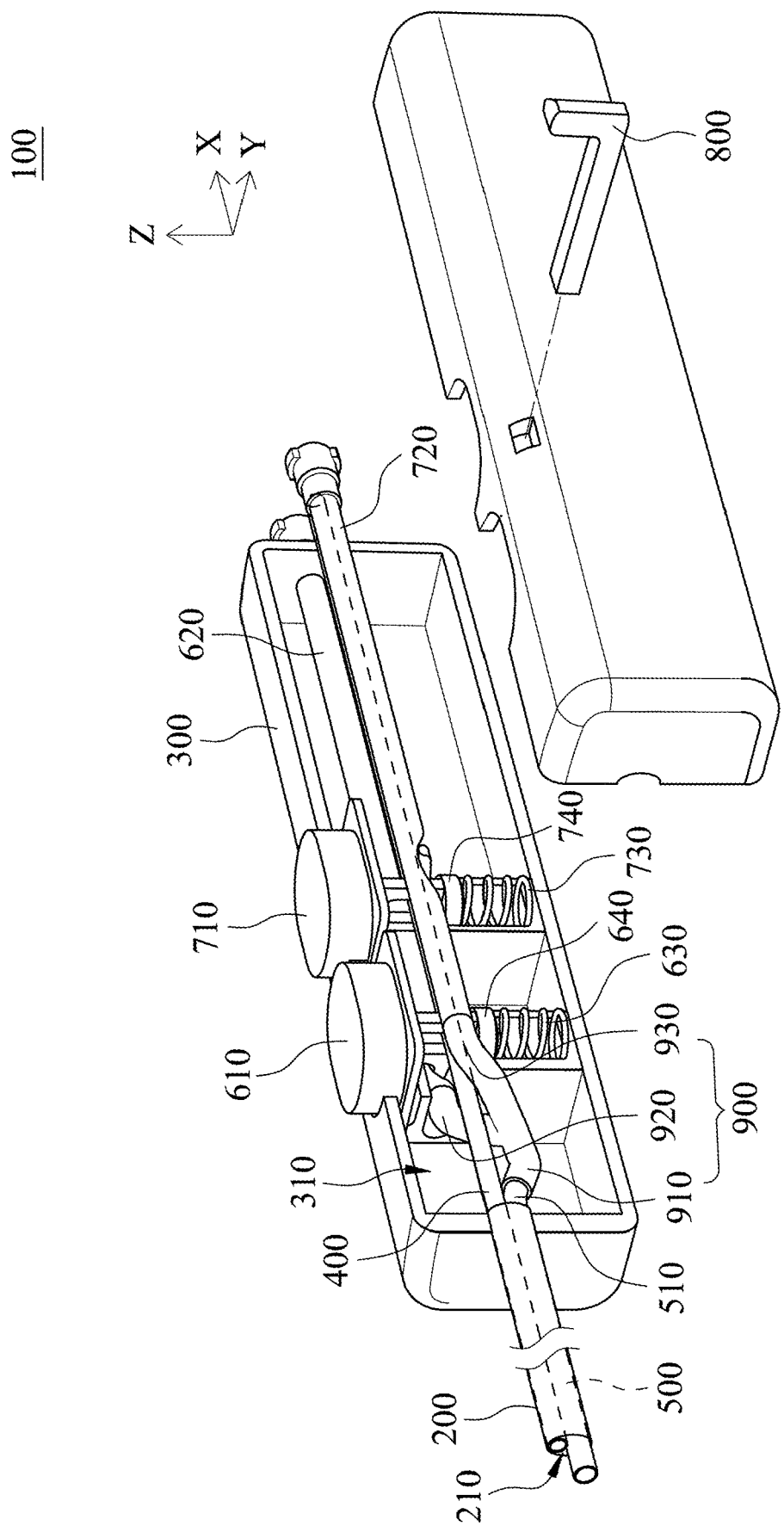
FIG. 3 is another exploded view showing the surgical irrigation and suction control apparatus of FIG. 1.
Figure 4B:
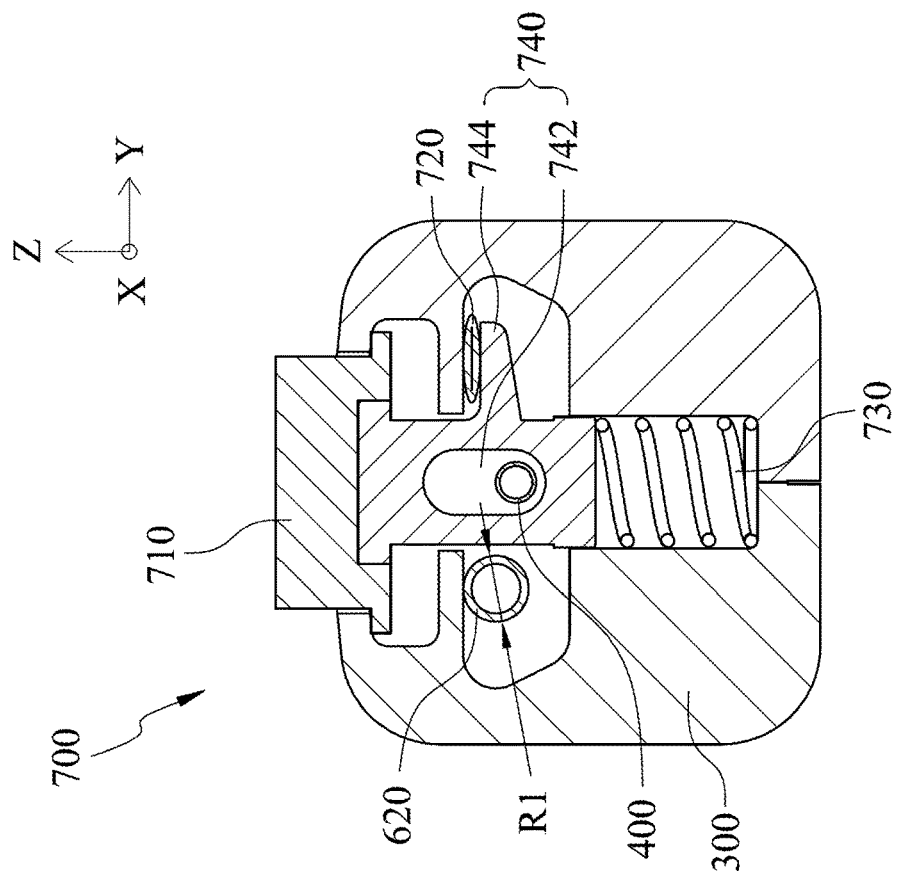
FIG. 4B is another cross-sectional view showing the surgical irrigation and suction control apparatus of FIG. 1.
Figure 4A:
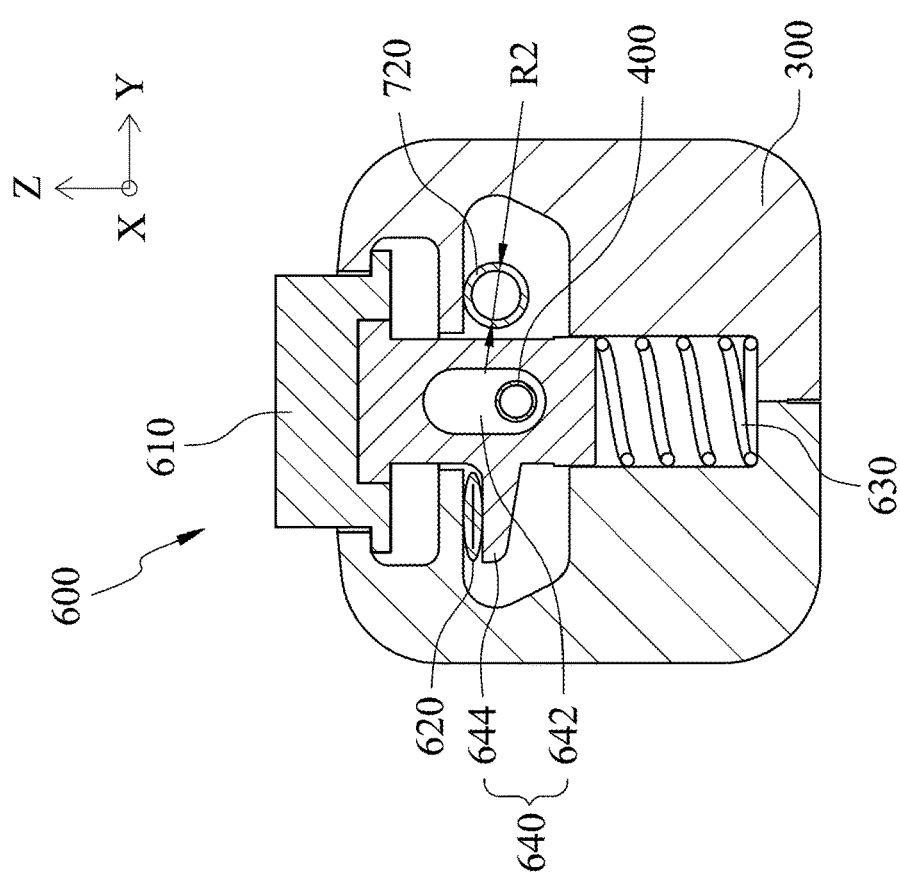
FIG. 4A is a cross-sectional view showing the surgical irrigation and suction control apparatus of FIG. 1.
Figure 10:
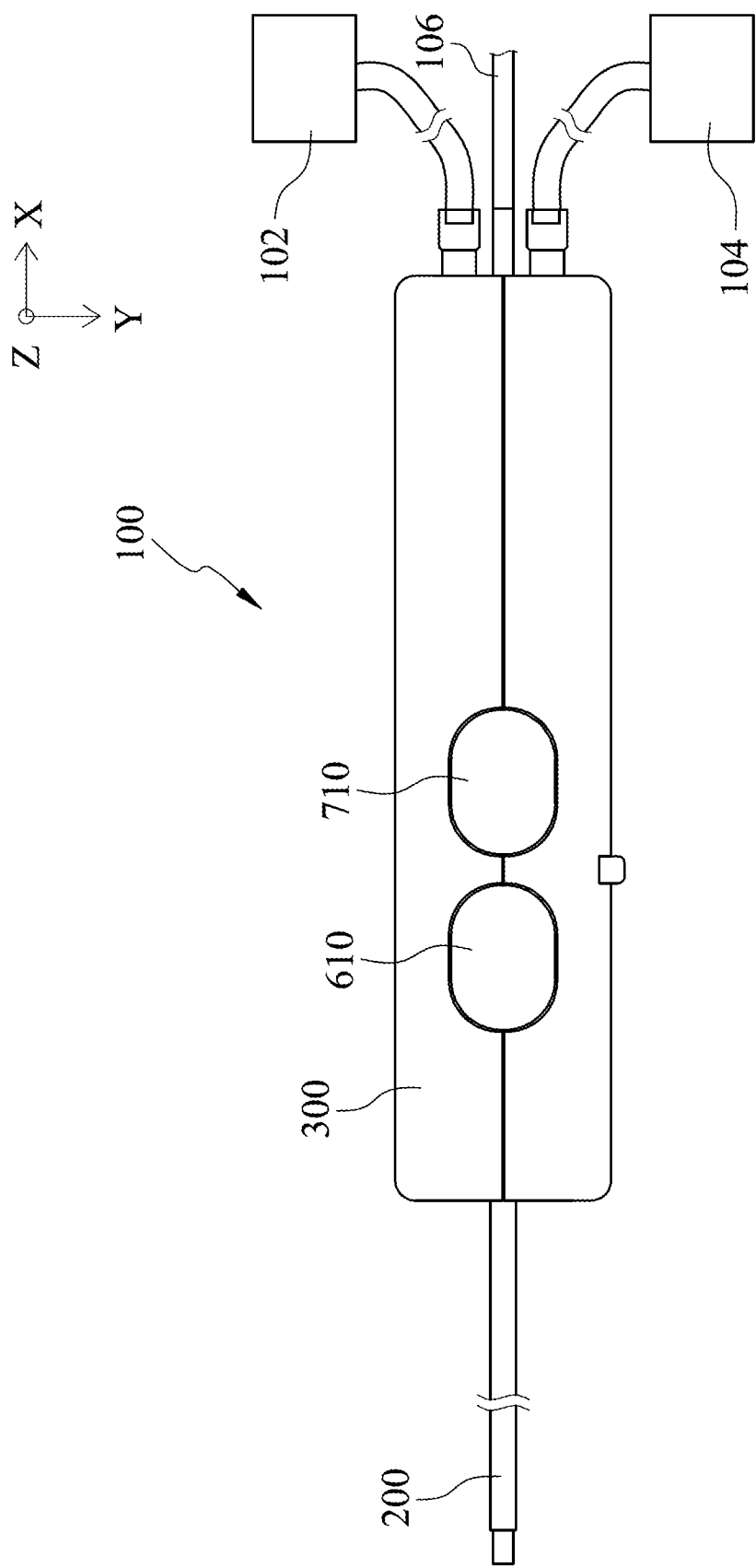
FIG. 10 is a top plan view showing the surgical irrigation and suction control apparatus of FIG. 1.

FIG. 1 is a schematic view showing a surgical irrigation and suction control apparatus 100 according to one embodiment of the present disclosure; FIG. 2 is an exploded view showing the surgical irrigation and suction control apparatus 100 of FIG. 1; FIG. 3 is another exploded view showing the surgical irrigation and suction control apparatus 100 of FIG. 1; FIG. 4A is a cross-sectional view showing the surgical irrigation and suction control apparatus 100 of FIG. 1; FIG. 4B is another cross-sectional view showing the surgical irrigation and suction control apparatus 100 of FIG. 1; and FIG. 10 is a top plan view showing the surgical irrigation and suction control apparatus 100 of FIG. 1. The surgical irrigation and suction control apparatus 100 is connected to an irrigation device 102 and a suction device 104. The surgical irrigation and suction control apparatus 100 includes a flexible cannula 200, a grip 300, a first tube 400, a second tube 500, an irrigation control unit 600, a suction control unit 700, a plug 800 and a partitioning member 900.

The flexible cannula 200 includes an inner space 210, front opening 220 and a connecting end 230. The front opening 220 and the connecting end 230 are located at opposite ends of the flexible cannula 200. The flexible cannula 200 is in a hollow cylindrical shape. The flexible cannula 200 is flexible and can be curved by a force.

The grip 300 is connected to the connecting end 230 of the flexible cannula 200. The grip 300 includes an accommodating space 310, a first positioning seat 320 and a second positioning seat 330. The accommodating space 310 is communicated with the inner space 210. The first positioning seat 320 is disposed in the accommodating space 310. The first positioning seat 320 includes a first positioning slot 322 and a first supporting portion 324, and the first positioning slot 322 is in a cylindrical shape. In addition, the second positioning seat 330 is disposed in the accommodating space 310. The second positioning seat 330 includes a second positioning slot 332 and a second supporting portion 334, and the second positioning slot 332 is in a cylindrical shape. The first positioning seat 320 is parallel to the second positioning seat 330, and the first positioning seat 320 and the second positioning seat 330 are separated by a second distance D2.

The first tube 400 is through the inner space 210 and the accommodating space 310. The endoscope 106 is disposed through the first tube 400. The first tube 400 includes a proximal opening 410 and a first distal opening 420. The first distal opening 420 is aligned to the front opening 220 of the flexible cannula 200. The endoscope 106 may be penetrated from the proximal opening 410 to the first distal opening 420. In the present disclosure, the flexible cannula 200, the first tube 400 and the second tube 500 are made from flexible material and can be curved, so that the operating range of the surgical irrigation and suction control apparatus 100 can be increased in the human body.

The second tube 500 includes a connecting portion 510 and a second distal opening 520. The connecting portion 510 and the second distal opening 520 are located at opposite ends of the second tube 500. The second tube 500 is through the inner space 210, and the connecting portion 510 of the second tube 500 is located in the accommodating space 310. The second distal opening 520 and the front opening 220 are separated by a first distance D1.

The irrigation control unit 600 includes an irrigation switch 610, an irrigation tube 620, a first elastic member 630 and a first supporting member 640. The irrigation switch 610 may be a push button. The irrigation switch 610 is disposed on the grip 300. The irrigation tube 620 is flexible, and one end of the irrigation tube 620 is connected to the irrigation device 102. The irrigation switch 610 is actuated to change a diameter R1 of the irrigation tube 620. The first elastic member 630 is disposed in the first positioning slot 322 of the first positioning seat 320. The first elastic member 630 can be a compression spring. The first supporting member 640 is located in the accommodating space 310. Two ends of the first supporting member 640 are connected to the first elastic member 630 and the irrigation switch 610, respectively. The first supporting member 640 has a first hole 642 and a first protruding portion 644. The irrigation tube 620 is located between the first protruding portion 644 and the first supporting portion 324.

The suction control unit 700 includes a suction switch 710, a suction tube 720, a second elastic member 730 and a second supporting member 740. The suction switch 710 may be a push button. The suction switch 710 is disposed on the grip 300, and the suction switch 710 is actuated to change a diameter R2 of the suction tube 720. The suction tube 720 is flexible, and one end of the suction tube 720 is connected to the suction device 104. The second elastic member 730 is disposed in the second positioning slot 332 of the second positioning seat 330. The second elastic member 730 can be a compression spring. The second supporting member 740 is located in the accommodating space 310. Two ends of the second supporting member 740 are connected to the second elastic member 730 and the suction switch 710, respectively. The second supporting member 740 has a second hole 742 and a second protruding portion 744. The first hole 642 is corresponding to the second hole 742, and the first tube 400 is through the first hole 642 and the second hole 742. This structure can effectively reduce the volume of accommodating space 310 and the weight of the grip 300, so that it is easy to take and operate. The suction tube 720 is located between the second protruding portion 744 and the second supporting portion 334. Thus, the surgical irrigation and suction control apparatus 100 has simple structure and can be fabricated by a simple process at low cost. Therefore, it is favorable for mass production and can be easily used for any operator.

The plug 800 is removably connected to the grip 300 for positioning the irrigation switch 610 or the suction switch 710. The plug 800 can be a L-shaped lever and is easily used by the physician or doctor.

The partitioning member 900 includes three terminals 910, 920, 930 which are connected to the connecting portion 510 of the second tube 500, the other end of the irrigation tube 620 and the other end of the suction tube 720, respectively. The partitioning member 900 is a Y-tube. In detail, the partitioning member 900 has a Y shape when viewed from a Z-axis direction and has a curved shape when viewed from a Y-axis direction. The partitioning member 900 is adjacent to the first tube 400. The first tube 400 is located between the terminal 920 and the terminal 930 when viewed from an X-axis direction. In other words, the first tube 400 is located between the irrigation tube 620 and the suction tube 720 when viewed from the X-axis direction. Moreover, an outer diameter of the second tube 500 is equal to an inner diameter of the terminal 910. An inner diameter of the other end of the irrigation tube 620 is equal to an outer diameter of the terminal 920. An inner diameter of the other end of the suction tube 720 is equal to an outer diameter of the terminal 930. The terminal 910 is connected to the connecting portion 510. The terminal 920 of the partitioning member 900 is connected to the other end of the irrigation tube 620. The terminal 930 is connected to the other end of the suction tube 720. The terminal 920 and 930 have the same height, and there is a height difference between the terminal 910 and the terminal 920 so as to effectively utilize the space in the grip 300 and reduce the volume of the grip 300.

Figure 5:
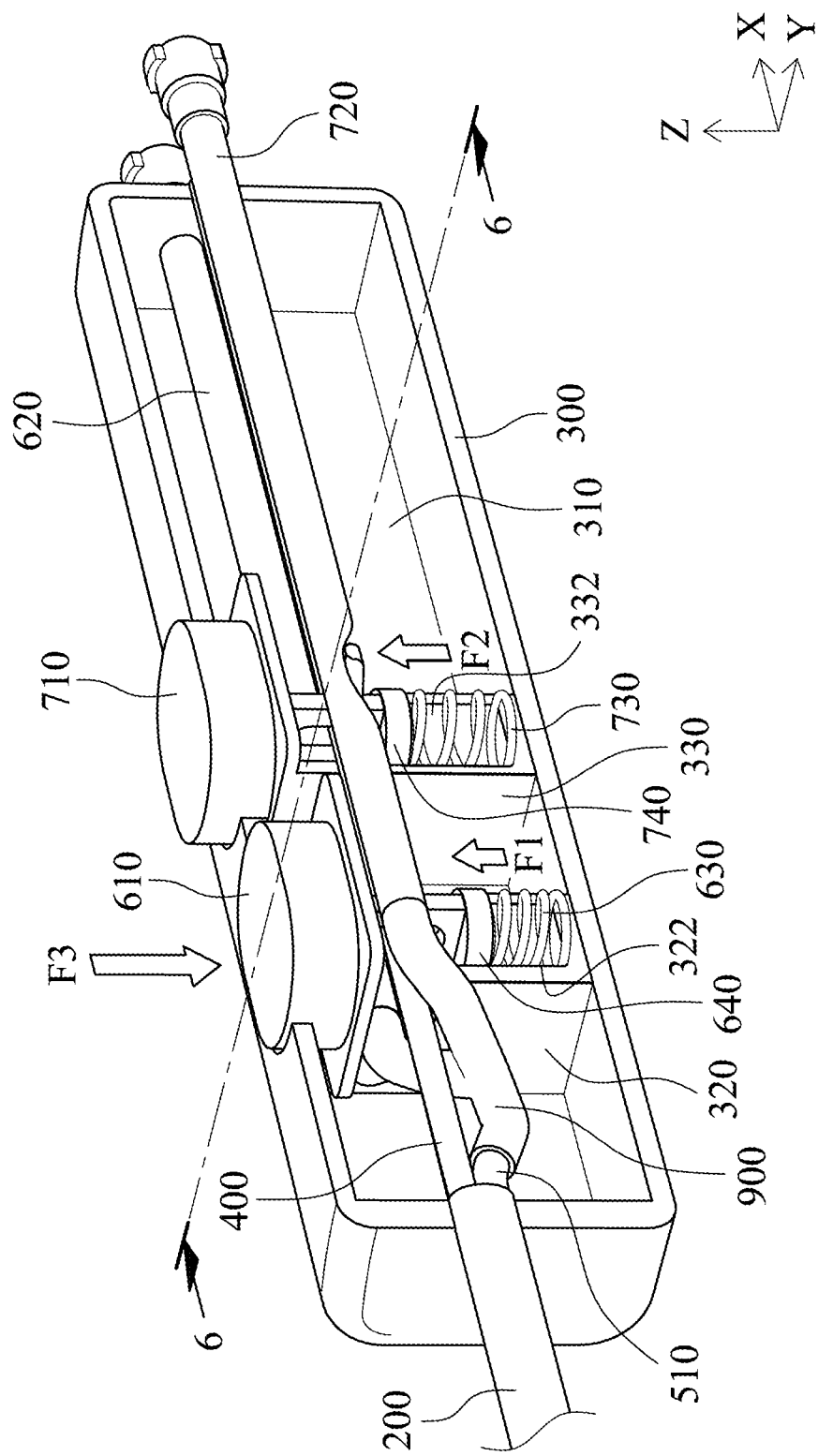
FIG. 5 is another schematic view showing the surgical irrigation and suction control apparatus of FIG. 1.
Figure 6:
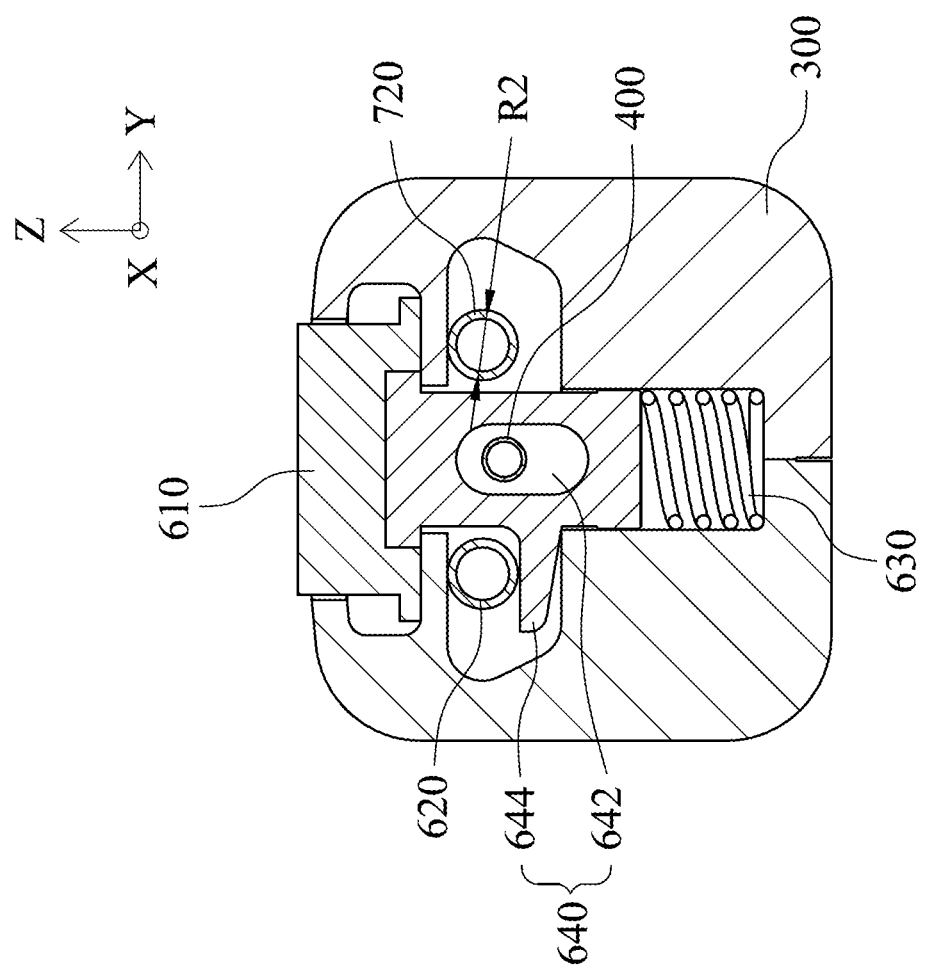
FIG. 6 is a cross-sectional view showing the surgical irrigation and suction control apparatus of FIG. 5.
Figure 7:
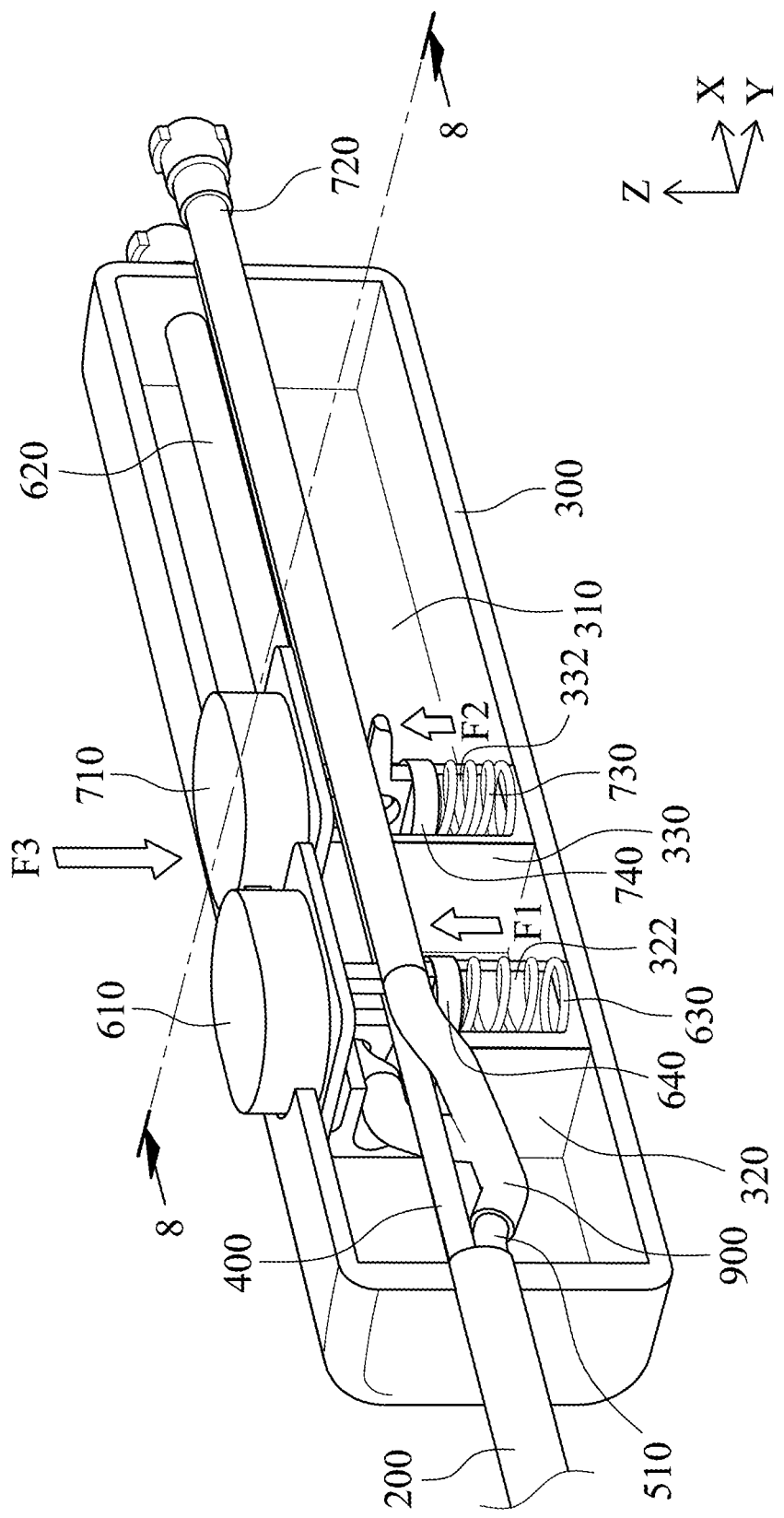
FIG. 7 is further another schematic view showing the surgical irrigation and suction control apparatus of FIG. 1.
Figure 8:
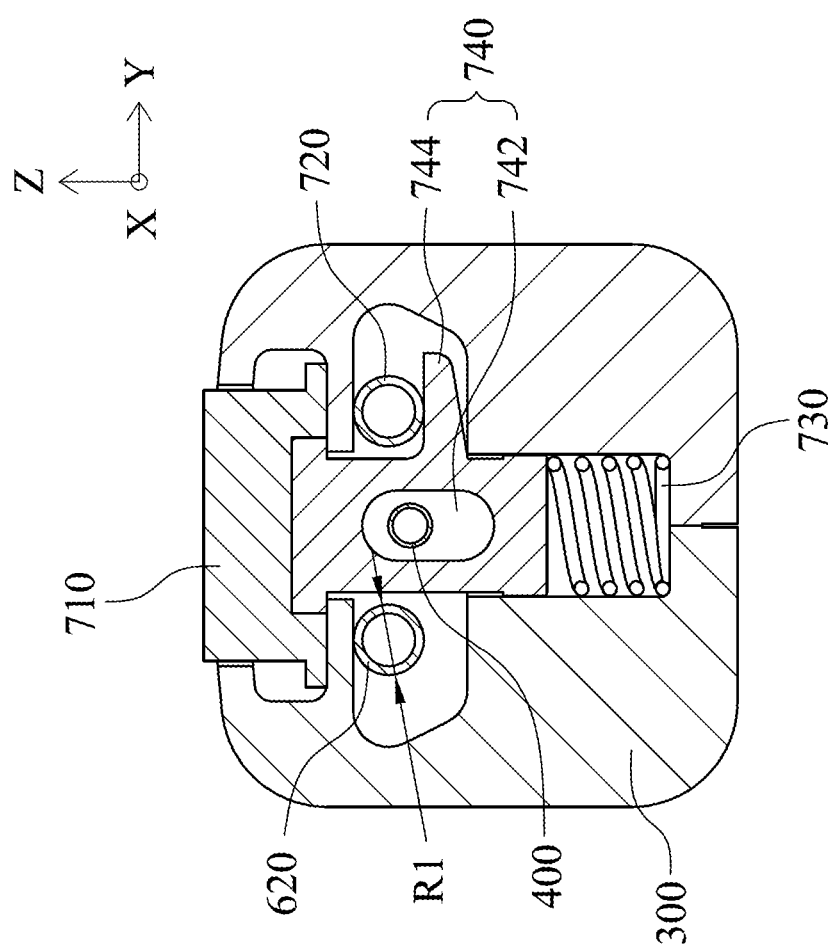
FIG. 8 is a cross-sectional view showing the surgical irrigation and suction control apparatus of FIG. 7.

FIG. 5 is another schematic view showing the surgical irrigation and suction control apparatus 100 of FIG. 1; FIG. 6 is a cross-sectional view showing the surgical irrigation and suction control apparatus 100 of FIG. 5; FIG. 7 is further another schematic view showing the surgical irrigation and suction control apparatus 100 of FIG. 1; and FIG. 8 is a cross-sectional view showing the surgical irrigation and suction control apparatus 100 of FIG. 7.

In FIGS. 4A and 7, no external force being exerted on the irrigation switch 610. The first supporting member 640 is pushed by the first restoring force F1 of the first elastic member 630 for flattening the irrigation tube 620 by the first protruding portion 644 of the first supporting member 640 thereby decreasing the diameter R1 of the irrigation tube 620.

In FIGS. 4B and 5, no external force being exerted on the suction switch 710. The second supporting member 740 is pushed by the second restoring force F2 of the second elastic member 730 for flattening the suction tube 720 by the second protruding portion 744 of the second supporting member 740 thereby decreasing the diameter R2 of the suction tube 720.

In FIGS. 5 and 7, the first elastic member 630 is disposed in the first positioning slot 322 of the first positioning seat 320 for applying a first restoring force F1. The second elastic member 730 is disposed in the second positioning slot 332 of the second positioning seat 330 for applying a second restoring force F2.

In FIGS. 5 and 6, the first supporting member 640 is moved in a first direction by exerting an external force F3 provided by the irrigation switch 610. The first direction represents a negative Z-axis direction. The external force F3 given by the physician is greater than the first restoring force F1 given by the first elastic member 630. On the other hand, if the external force F3 is smaller than the first restoring force F1, the first supporting member 640 is moved in a second direction by exerting the first restoring force F1 from the first elastic member 630. The second direction represents a positive Z-axis direction.

In FIGS. 7 and 8, the second supporting member 740 is moved in the first direction by exerting the external force F3 which is provided by the suction switch 710. The external force F3 given by the physician is greater than the second restoring force F2 given by the second elastic member 730. On the other hand, if the external force F3 is smaller than the second restoring force F2, the second supporting member 740 is moved in the second direction by exerting the second restoring force F2 from the second elastic member 730. Most importantly, the irrigation switch 610 and the suction switch 710 are not actuated simultaneously. In other words, irrigation tube 620 and the suction tube 720 are not opened at the same time.

Figure 9:
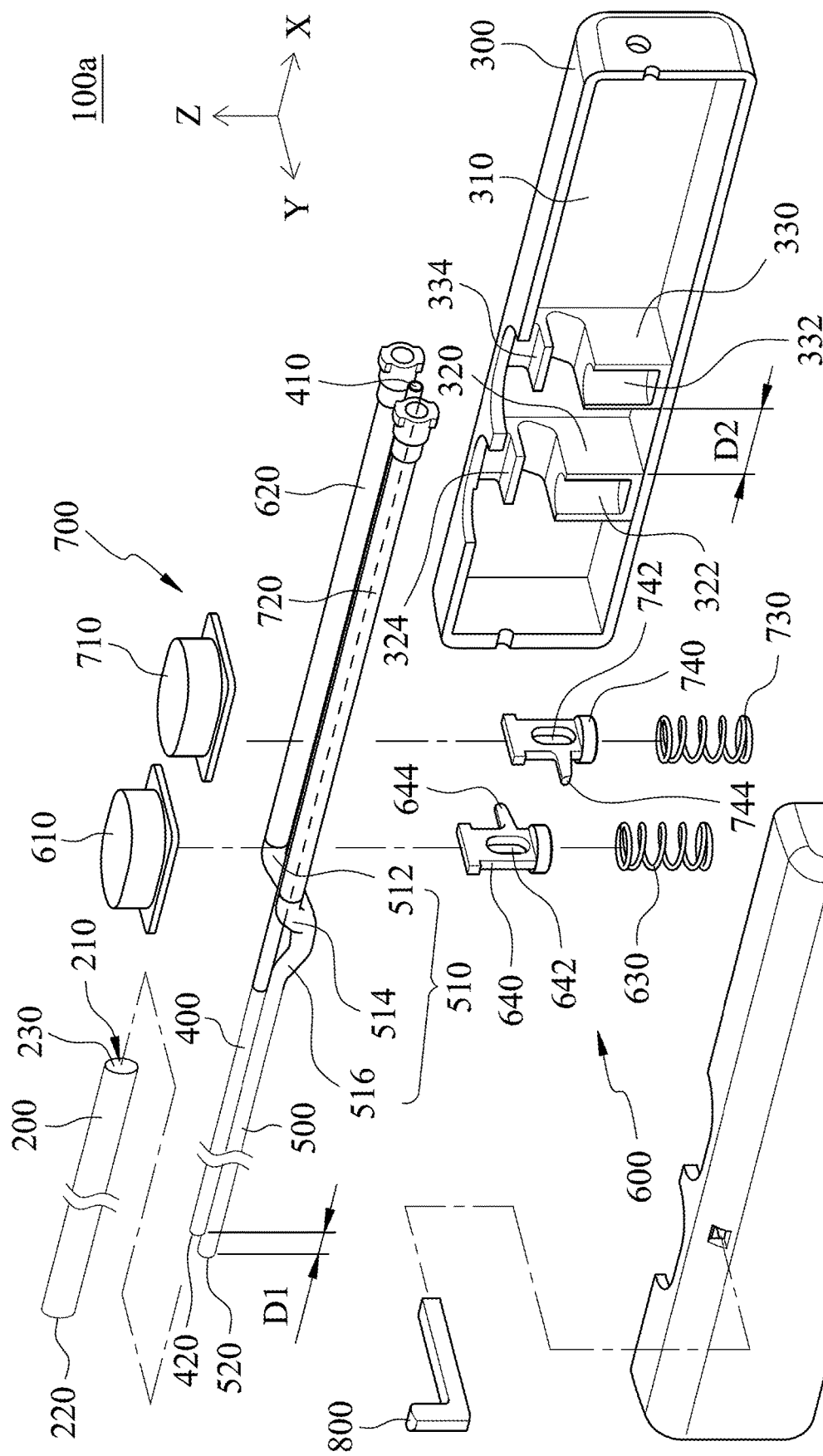
FIG. 9 is a schematic view showing a surgical irrigation and suction control apparatus according to another embodiment of the present disclosure.

FIG. 9 is a schematic view showing a surgical irrigation and suction control apparatus 100a according to another embodiment of the present disclosure. In FIG. 9, the connecting portion 510 of the second tube 500 has a first opening end 512, a second opening end 514 and a lower end 516. The first opening end 512 and the second opening end 514 have the same height, and there is a height difference between the lower end 516 and the first opening end 512, thereby effectively utilizing the space in the grip 300 and reducing the volume of the grip 300. An inner diameter of the second tube 500 is equal to or smaller than an inner diameter of the irrigation tube 620 and an inner diameter of the suction tube 720. The irrigation tube 620 is connected between the first opening end 512 of the connecting portion 510 of the second tube 500 and the irrigation device 102. The suction tube 720 is connected between the second opening end 514 of the connecting portion 510 of the second tube 500 and the suction device 104.

Figure 11:
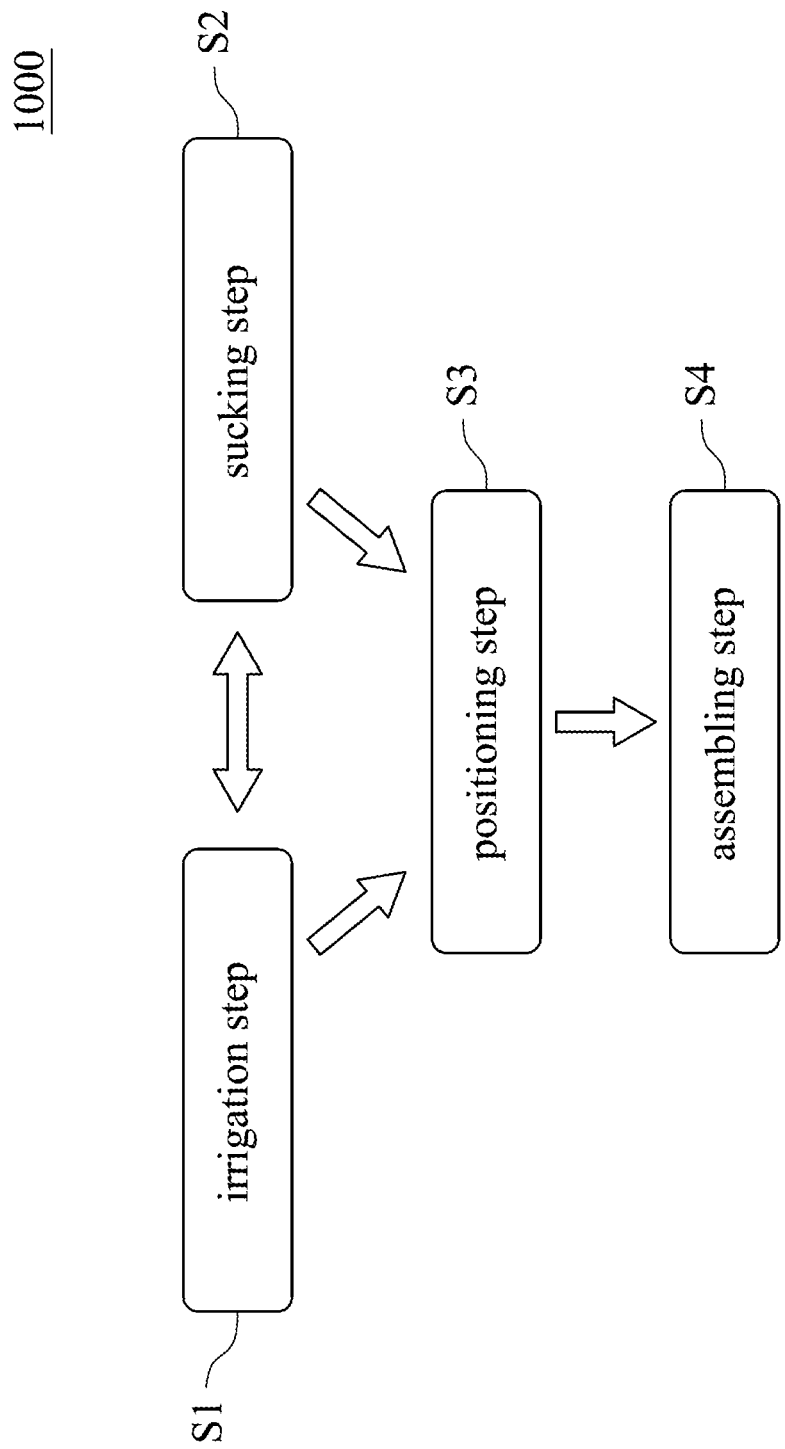
FIG. 11 is a flow chart showing a surgical irrigation and suction control method according to one embodiment of the present disclosure.

FIG. 11 is a flow chart showing a surgical irrigation and suction control method 1000 according to one embodiment of the present disclosure. The surgical irrigation and suction control method 1000 is for operating the surgical irrigation and suction control apparatus 100, 100a. The surgical irrigation and suction control method 1000 includes an irrigating step S1, a sucking step S2, a positioning step S3 and an assembling step S4. The irrigating step S1 is for pressing an irrigation switch 610 to increase a diameter R1 of an irrigation tube 620 thereby communicating an irrigation device 102 with a second tube 500 via the irrigation tube 620. The sucking step S2 is for pressing a suction switch 710 to increase a diameter R2 of a suction tube 720 thereby communicating a suction device 104 with the second tube 500 via the suction tube 720. The irrigating step S1 and the sucking step S2 are not operated simultaneously. The positioning step S3 is for plugging a plug 800 to the grip 300 to position the irrigation switch 610 or the suction switch 710. The assembling step S4 is for installing an endoscope 106 through the first tube 400. The assembling step S4 can be performed before, during, and/or after the irrigating step S1 or the sucking step S2. By the surgical irrigation and suction control method 1000, irrigation or suction to a surgical site can be effectively performed as well as maintaining clear viewing range through the endoscope 106 during a surgical procedure.

Figure 12A:
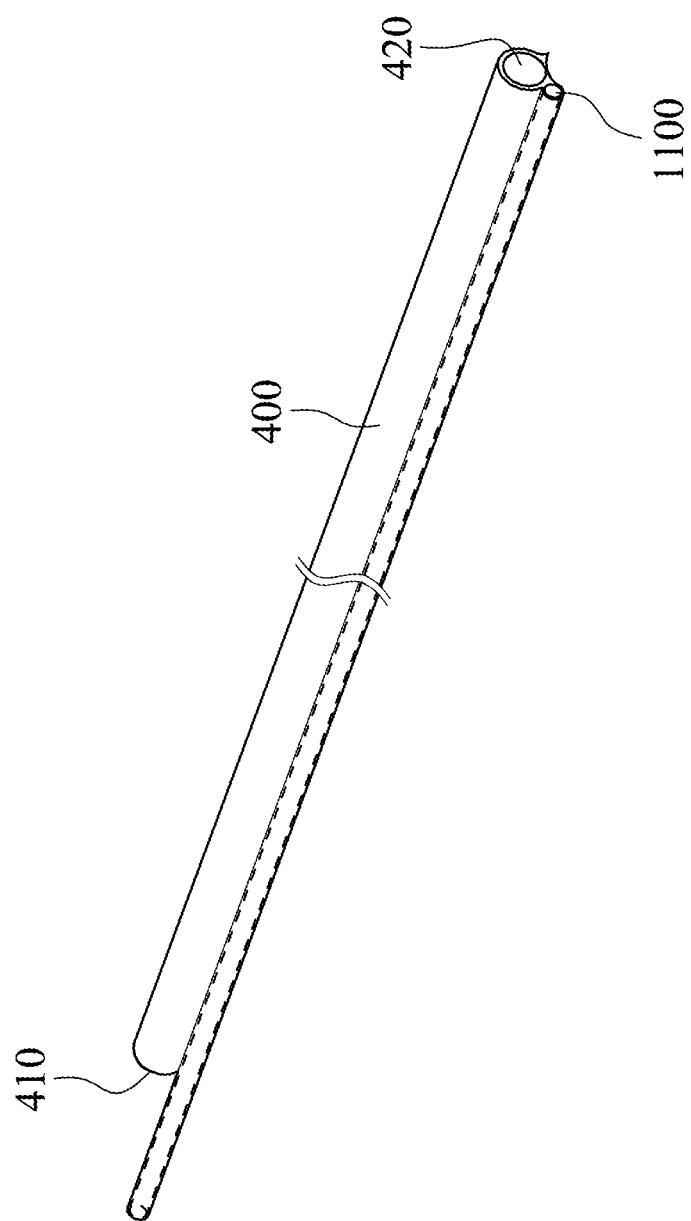
FIG. 12A is a schematic view showing a first tube and a third tube of a surgical irrigation and suction control apparatus according to further another embodiment of the present disclosure.
Figure 12B:
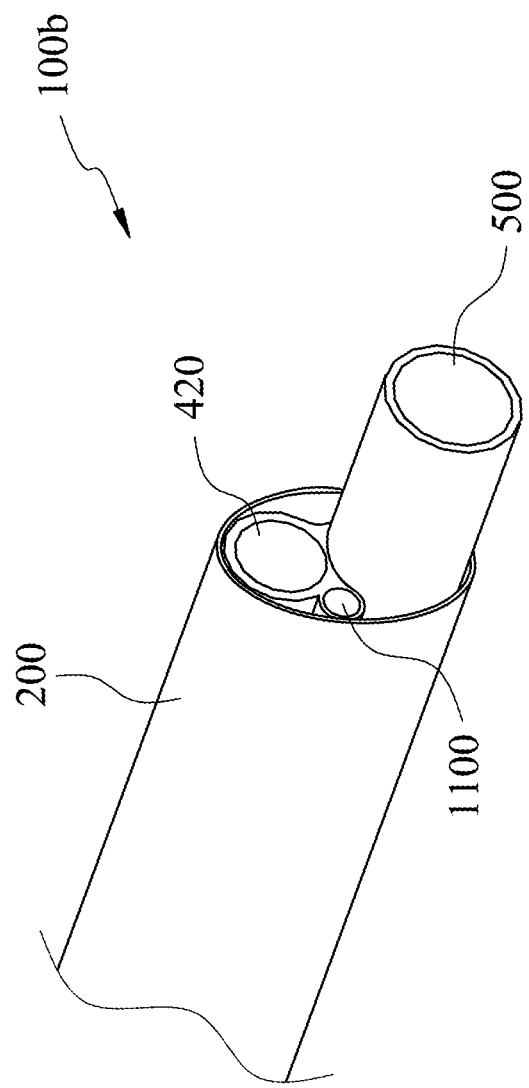
FIG. 12B is a schematic view shoving one end of the surgical irrigation and suction control apparatus of FIG. 12A.
Figure 12C:
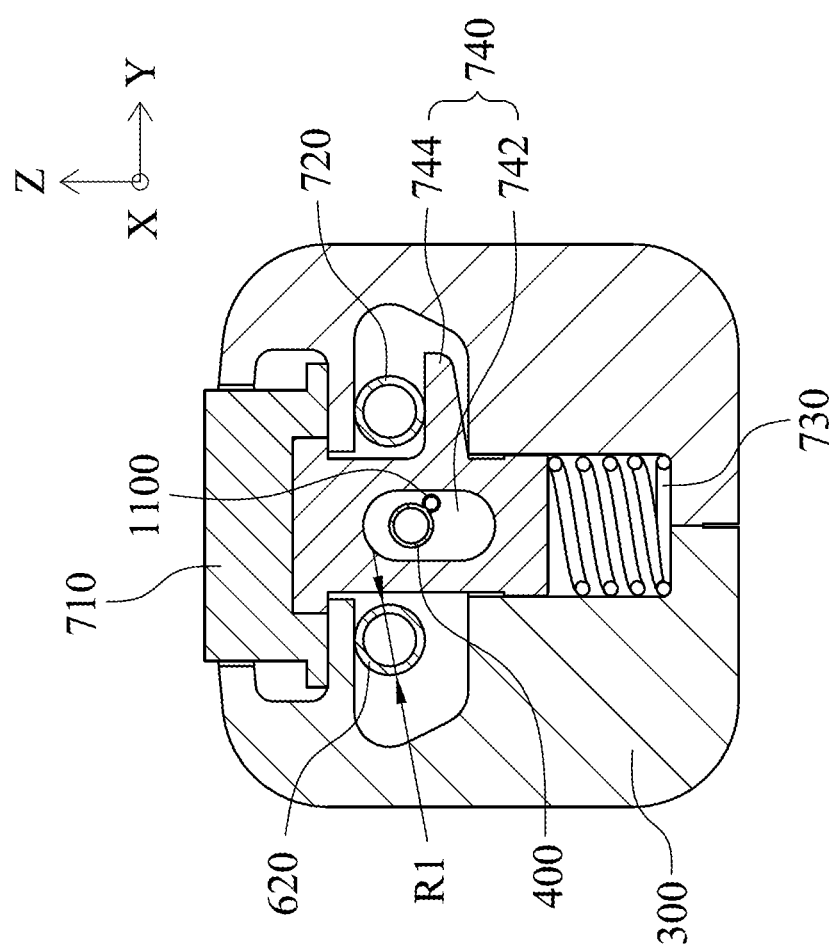
FIG. 12C is a cross-sectional view showing the surgical irrigation and suction control apparatus of FIG. 12A.
Figure 12D:
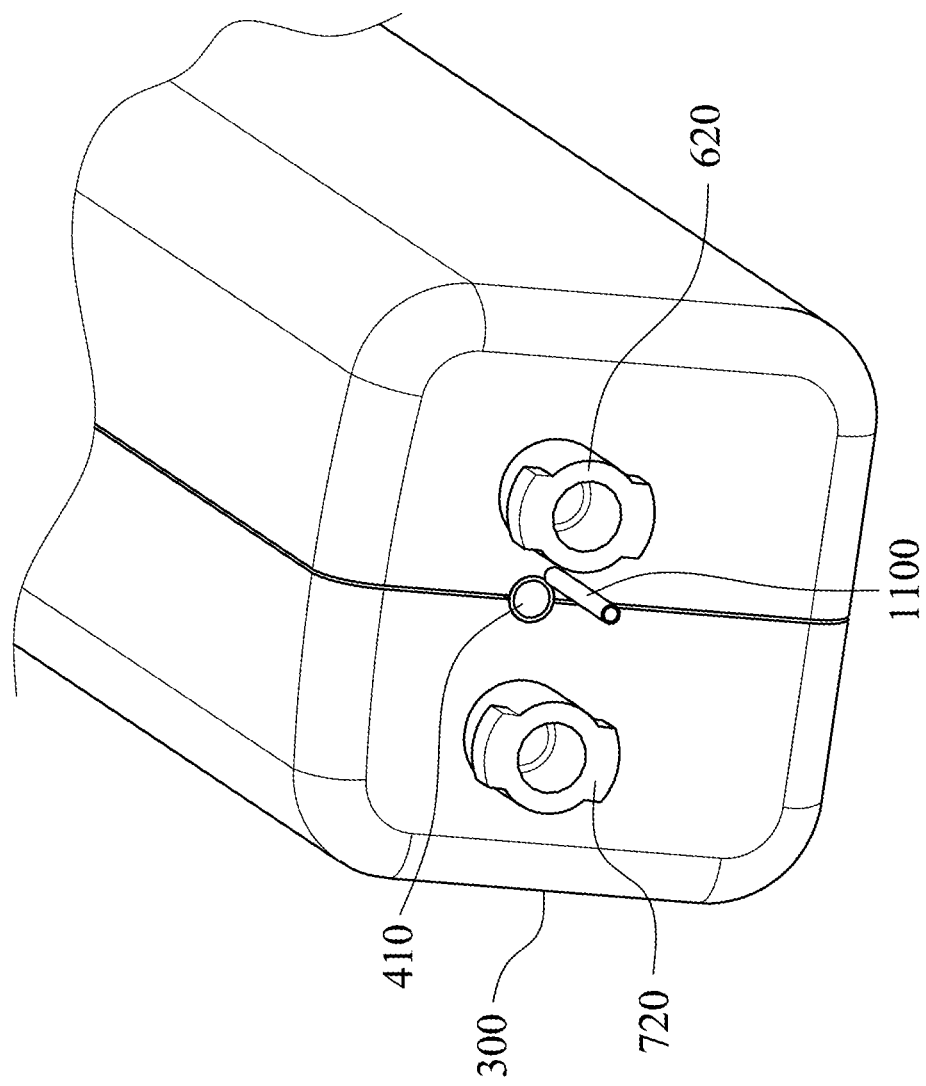
FIG. 12D is a schematic view showing the other end of the surgical irrigation and suction control apparatus of FIG. 12A.

FIG. 12A is a schematic view showing a first tube 400 and a third tube 1100 of a surgical irrigation and suction control apparatus 100b according to further another embodiment of the present disclosure; FIG. 12B is a schematic view showing one end of the surgical irrigation and suction control apparatus 100b of FIG. 12A; FIG. 12C is a cross-sectional view showing the surgical irrigation and suction control apparatus 100b of FIG. 12A; and FIG. 12D is a schematic view showing the other end of the surgical irrigation and suction control apparatus 100b of FIG. 12A. The surgical irrigation and suction control apparatus 100b includes a flexible cannula 200, a grip 300, a first tube 400, a second tube 500, a third tube 1100, an irrigation control unit 600, a suction control unit 700, a plug 800 and a partitioning member 900.

In FIGS. 12A, 12B, 12C and 12D, the details of the flexible cannula 200, a first tube 400, a second tube 500, an irrigation control unit 600, a suction control unit 700, a plug 800 and a partitioning member 900 are the same as the flexible cannula 200, a first tube 400, a second tube 500, an irrigation control unit 600, a suction control unit 700, a plug 800 and a partitioning member 900 of FIG. 2, respectively. In FIGS. 12A, 12B, 12C and 12D, the surgical irrigation and suction control apparatus 100b further includes the third tube 1100 and the grip 300 having an instrument hole. One end of the third tube 1100 is disposed through the instrument hole and is located in the grip 300. The third tube 1100 is connected to the first tube 400. The first tube 400 includes a proximal opening 410 and a first distal opening 420. The third tube 1100 and the first tube 400 are parallel to each other. The other end of the third tube 1100 is disposed in the flexible cannula 200. An opening of the other end of the third tube 1100 and the first distal opening 420 of the first tube 400 are aligned with an opening of the flexible cannula 200. A surgical instrument can be disposed into the third tube 1100 which may be flexible. In addition, the flexible cannula 200, the first tube 400, the second tube 500 and the third tube 1100 may be all flexible for bending. Accordingly, the surgical irrigation and suction control apparatus 100b can be used to simultaneously control the surgical instrument and the endoscope 106 with the functions of surgical irrigation and suction.

Figure 13A:
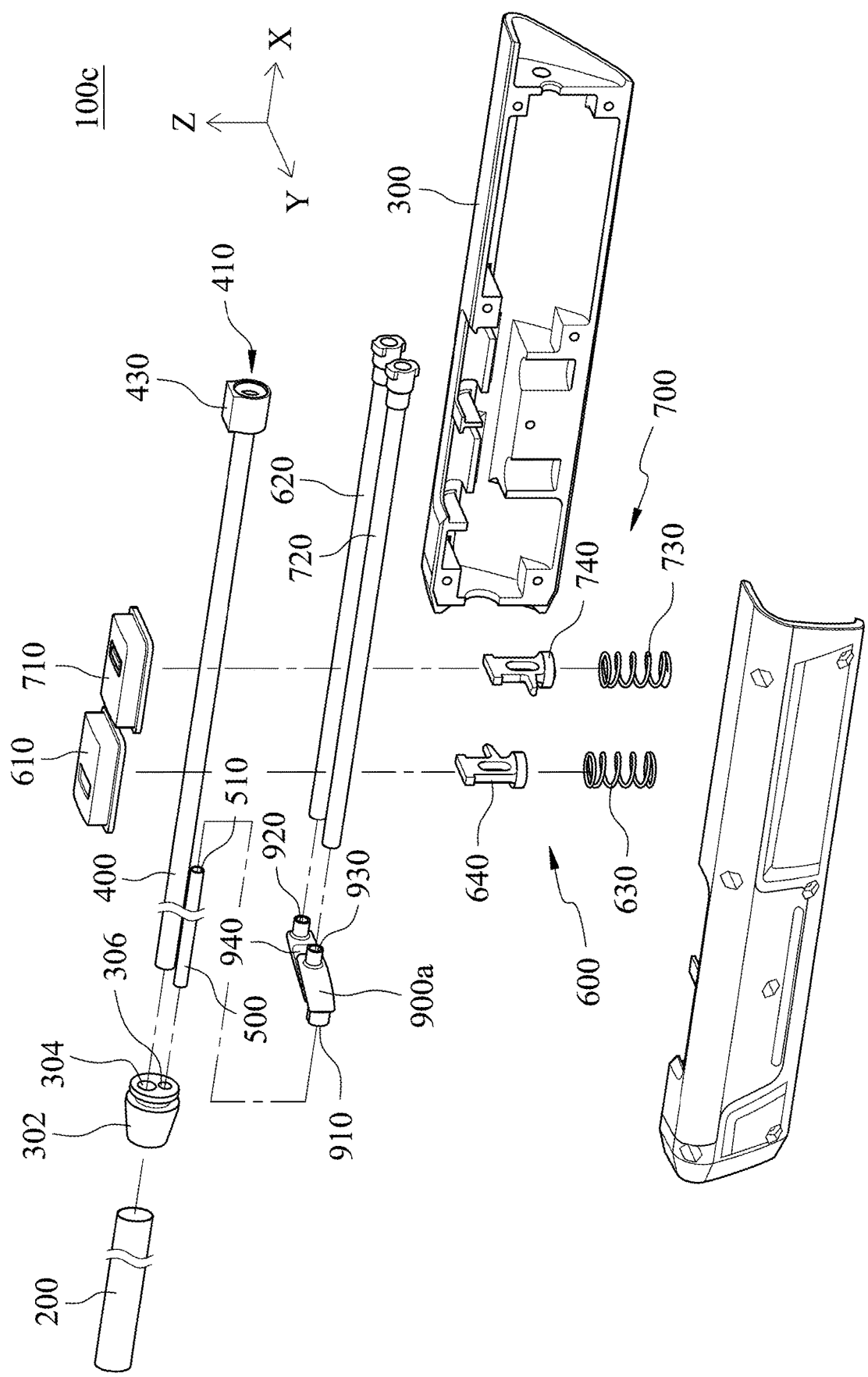
FIG. 13A is an exploded view showing a surgical irrigation and suction control apparatus according to still further another embodiment of the present disclosure.
Figure 13C:
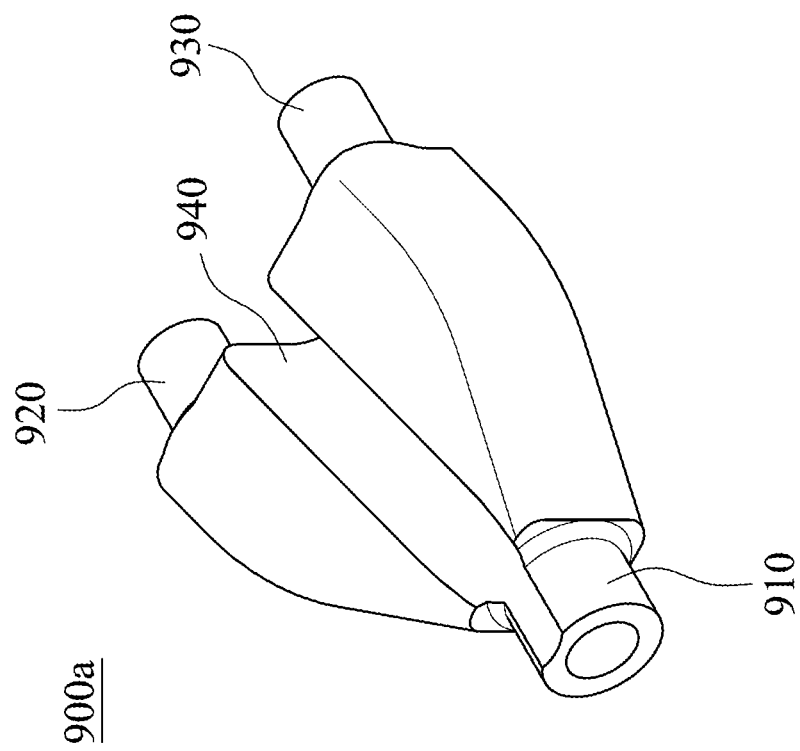
FIG. 13C is another schematic view showing the partitioning member of the surgical irrigation and suction control apparatus of FIG. 13A.
Figure 13B:
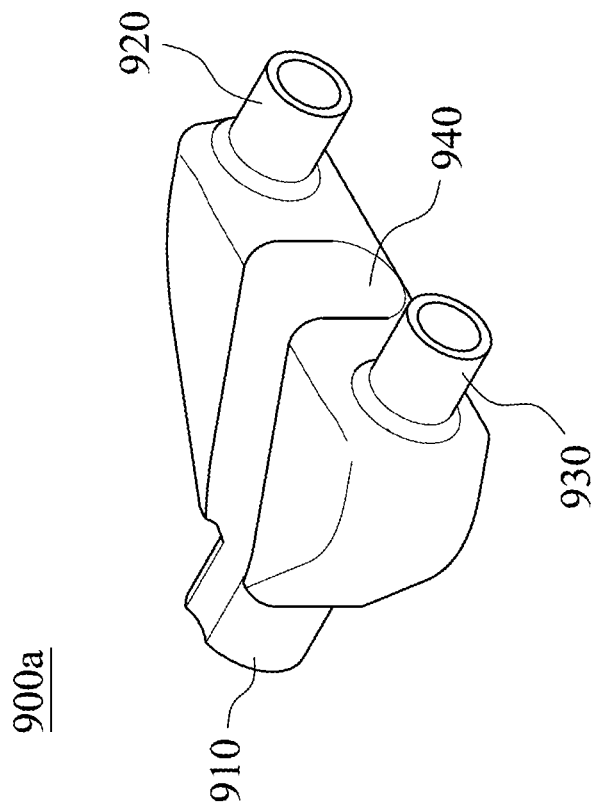
FIG. 13B is a schematic view showing a partitioning member of the surgical irrigation and suction, control apparatus of FIG. 13A.
Figure 13D:
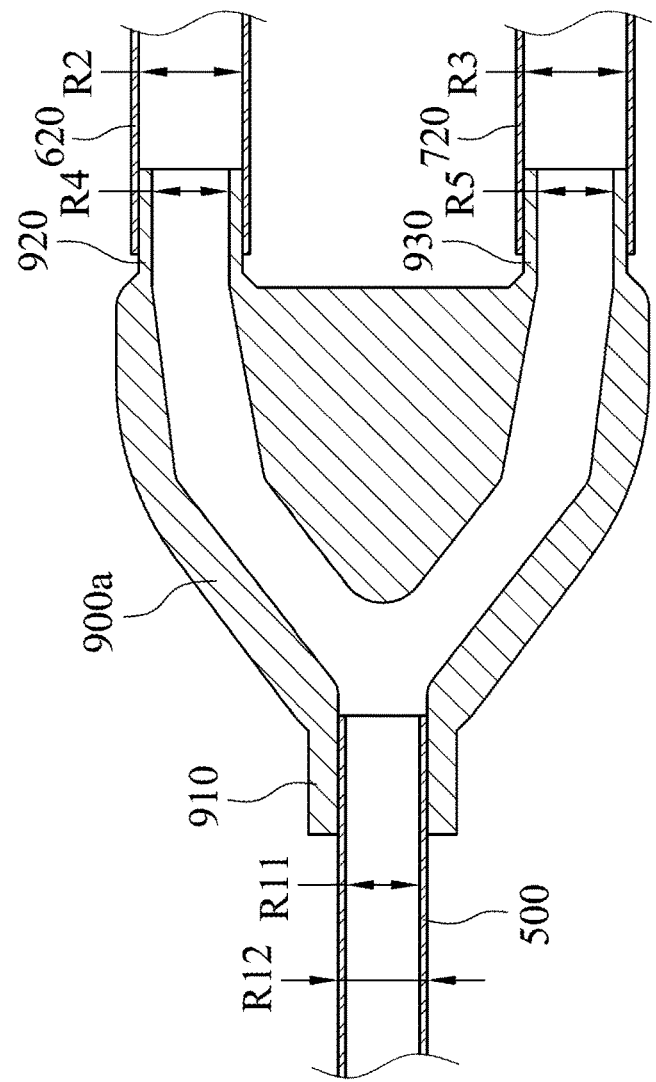
FIG. 13D is a top schematic view showing the partitioning member of FIG. 13B.
Figure 13E:
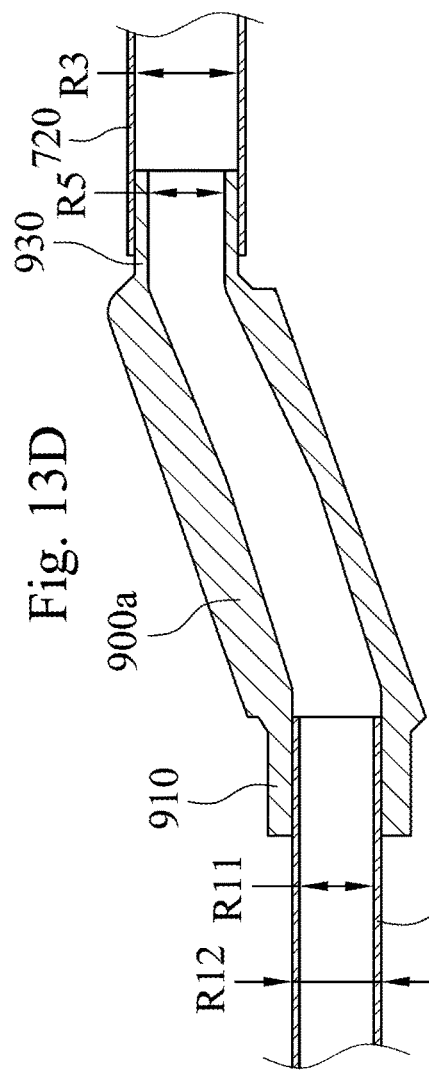
FIG. 13E is a side schematic view showing the partitioning member of FIG. 13B.
Figure 13F:
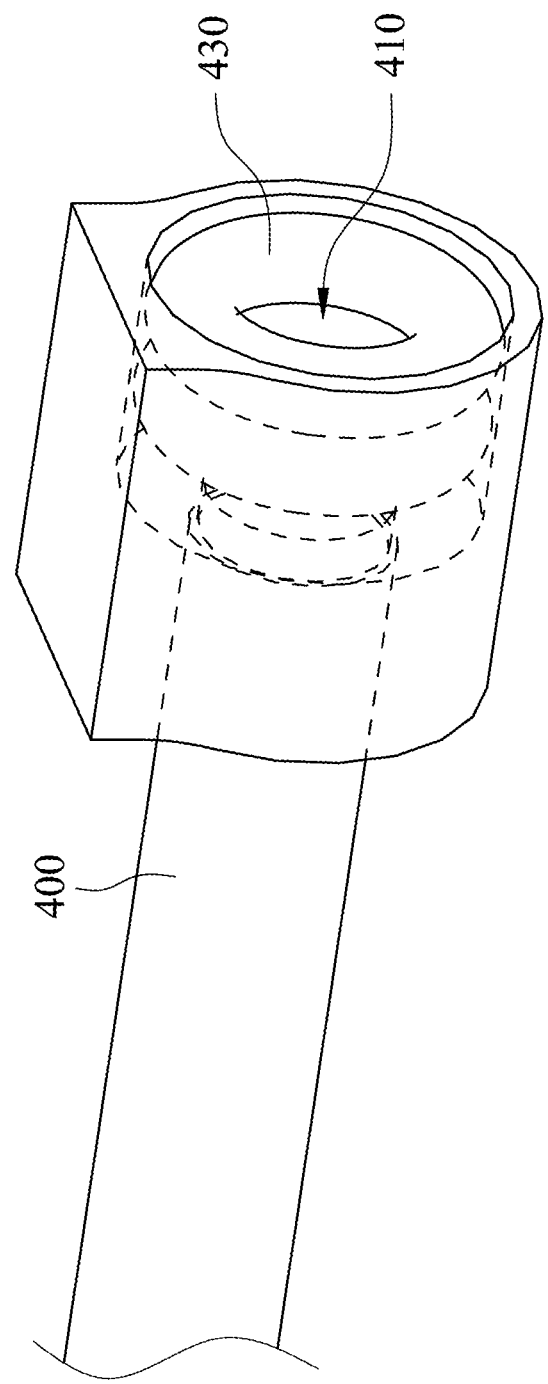
FIG. 13F is a schematic view showing an O-ring disposed on the first tube of FIG. 13A.

FIG. 13A is an exploded view showing a surgical irrigation and suction control apparatus 100c according to still further another embodiment of the present disclosure; FIG. 13B is a schematic view showing a partitioning member 900a of the surgical irrigation and suction control apparatus 100c of FIG. 13A; FIG. 13C is another schematic view showing the partitioning member 900a of the surgical irrigation and suction control apparatus 100c of FIG. 13A; FIG. 13D is a top schematic view showing the partitioning member 900a of FIG. 13B; FIG. 13E is a side schematic view showing the partitioning member 900a of FIG. 13B; and FIG. 13F is a schematic view showing an O-ring 430 disposed on the first tube 400 of FIG. 13A. The surgical irrigation and suction control apparatus 100c includes a flexible cannula 200, a grip 300a, a guiding member 302, a first tube 400, a second tube 500, an irrigation control unit 600, a suction control unit 700 and a partitioning member 900a.

In FIGS. 13A-13F, the details of the flexible cannula 200, the first tube 400, the second tube 500, the irrigation control unit 600 and the suction control unit 700 are the same as the flexible cannula 200, the first tube 400, the second tube 500, the irrigation control unit 600 and the suction control unit 700 of FIG. 2, respectively. In FIGS. 13A-13F, the surgical irrigation and suction control apparatus 100c further includes the grip 300a, the guiding member 302 and the partitioning member 900a. The guiding member 302 is connected between the flexible cannula 200 and the grip 300a. The guiding member 302 has two holes 304, 306 for positioning the first tube 400 and a second tube 500, respectively. The grip 300a has a triangular columnar shape so as to facilitate holding. The first tube 400 includes a proximal opening 410 and an O-ring 430. The O-ring 430 is disposed around the proximal opening 410. The endoscope 106 shown in FIG. 10 is movably connected to the O-ring 430 and passed through the proximal opening 410. In addition, the partitioning member 900a includes three terminals 910, 920, 930 and a guiding slot 940. The guiding slot 940 is located between the terminals 920, 930 and corresponding to the terminal 910. The first tube 400 can be positioned in the guiding slot 940. The three terminals 910, 920, 930 are connected to the connecting portion 510, the irrigation tube 620 and the suction tube 720, respectively. An outer diameter R12 of the second tube 500 is equal to an inner diameter of the terminal 910 and greater than an inner diameter R11 of the second tube 500. An inner diameter R2 of the irrigation tube 620 is equal to an outer diameter of the terminal 920 and greater than an inner diameter R4 of the terminal 920. The inner diameter R4 is greater than the inner diameter R11. An inner diameter R3 of the suction tube 720 is equal to an outer diameter of the terminal 930 and greater than an inner diameter R5 of the terminal 930. The inner diameter R5 is also greater than the inner diameter R11.

Figure 13G:
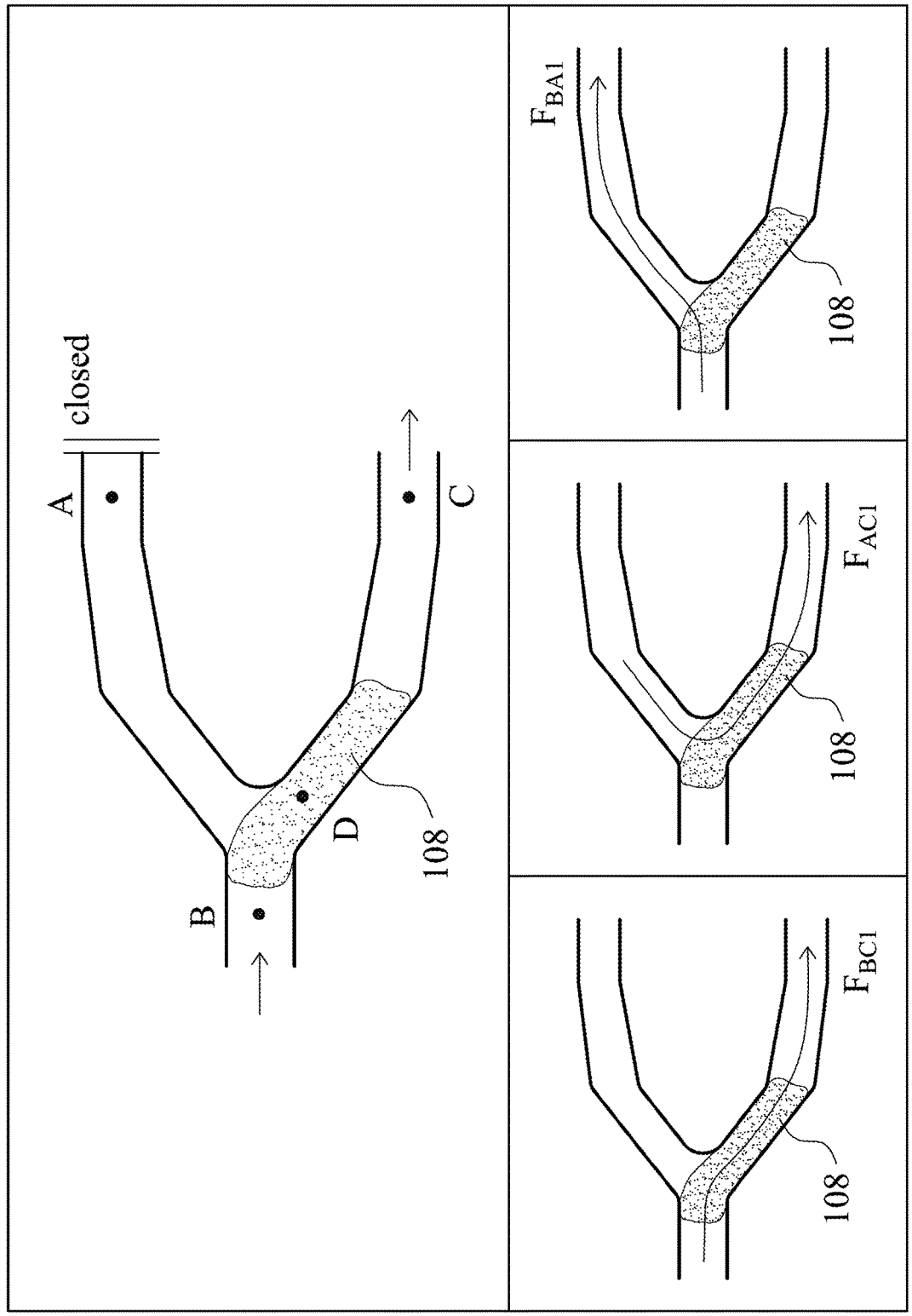
FIG. 13G is a schematic view showing a pressure distribution in the partitioning member of FIG. 13B as the irrigation tube being closed.
Figure 13H:
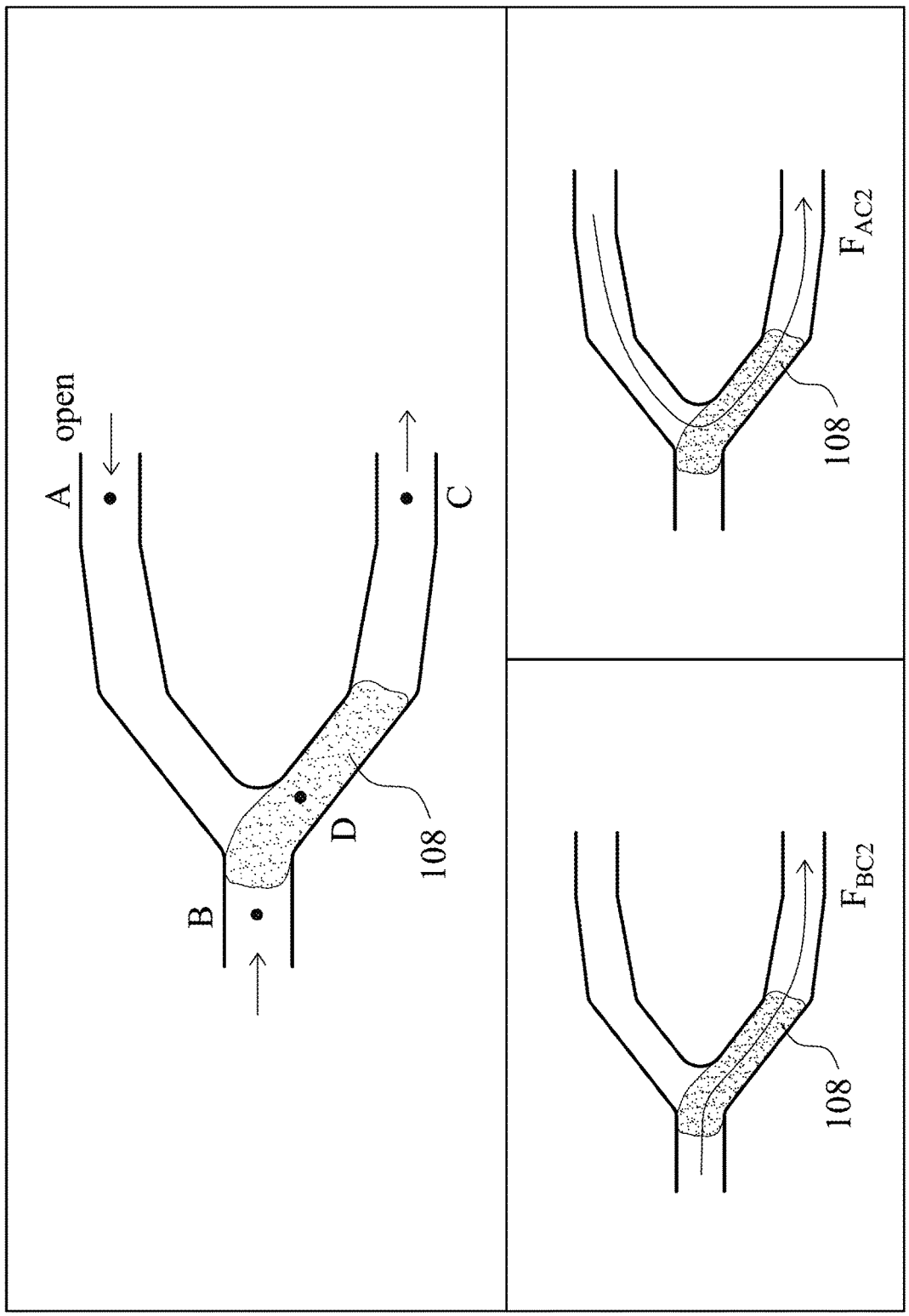
FIG. 13H is a schematic view showing another pressure distribution in the partitioning member of FIG. 13B as the irrigation tube being opened.

FIG. 13G is a schematic view showing a pressure distribution in the partitioning member 900a of FIG. 13B as the irrigation tube 620 being closed; and FIG. 13H is a schematic view showing another pressure distribution in the partitioning member 900a of FIG. 13B as the irrigation tube 620 being opened. When an object 108, such as a blood clot, is located between the position B and the position C, we assume that the pressure at the position B is 760 mmHg (1 atm), and the suction pressure of the suction tube 720 is about 200 mmHg. If the irrigation tube 620 is closed (i.e., only the suction switch 710 is actuated), the pressure at the position C is about 560 mmHg, and the pressure at the position A is about 600 mmHg. Accordingly, the total force applied to the object 108 is the sum of the forces $F_{BC1}$, $F_{AC1}$, and $F_{BA1}$, as shown in FIG. 13G. On the other hand, if the irrigation tube 620 is opened (i.e., the irrigation switch 610 and the suction switch 710 are actuated simultaneously), the pressure at the position C is about 560 mmHg, and the pressure at the position A is equal to or greater than 760 mmHg. Hence, the total force applied to the object 108 is the sum of the forces $F_{BC2}$ and $F_{AC2}$, as shown in FIG. 13H. The force $F_{AC2}$ is greater than the force $F_{AC1}$ because of the higher pressure at the position A, so that the object 108 is easily moved toward the suction tube 720 when the irrigation switch 610 and the suction switch 710 are actuated simultaneously.

According to the aforementioned embodiments and examples, the advantages of the present disclosure are described as follows.

1. The surgical irrigation and suction control apparatus and control method thereof of the present disclosure uses the irrigation control unit and the suction control unit thereby effectively providing irrigation or suction to a surgical site and maintaining clear through the endoscope during a surgical procedure.

2. The surgical irrigation and suction control apparatus and control method thereof of the present disclosure has simple structure and can be fabricated by a simple process at low cost. Therefore, it is favorable for mass production and can be easily used for any operator.

3. The flexible cannula, the first tube and the second tube of the present disclosure are made from flexible material, thus the operating range can be increased on the human body.

4. The volume of accommodating space and the weight of the grip can be effectively reduced, so that it is easy to take and operate.

5. The surgical irrigation and suction control apparatus and control method thereof of the present disclosure uses plural flexible tubes to simultaneously control the surgical instrument and the endoscope with the functions of surgical irrigation and suction.

6. When the irrigation switch and the suction switch are actuated simultaneously, the object in the partitioning member can be easily moved toward the suction tube according to different diameters of the connecting portion, the partitioning member, the irrigation tube and the suction tube.

7. There is a height difference between the terminals of the partitioning member so as to effectively utilize the space in the grip and reduce the volume of the grip.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A surgical irrigation and suction control apparatus configured to connect to an irrigation device and a suction device, the surgical irrigation and suction control apparatus comprising:
    a flexible cannula comprising an inner space;
    a grip connected to the flexible cannula and comprising an accommodating space communicating with the inner space;
    a first tube passed through the inner space and the accommodating space;
    a second tube comprising a connecting portion, wherein the second tube is through the inner space, and the connecting portion of the second tube is located in the accommodating space;
    an irrigation control unit comprising an irrigation switch and an irrigation tube, wherein the irrigation tube is flexible, a first end of the irrigation tube is connected to the irrigation device, the irrigation switch is disposed on the grip, and the irrigation switch is actuated to change a diameter of the irrigation tube;
    a suction control unit comprising a suction switch and a suction tube, wherein the suction tube is flexible, a first end of the suction tube is connected to the suction device, the suction switch is disposed on the grip, and the suction switch is actuated to change a diameter of the suction tube; and
    a partitioning member having three terminals which are connected to the connecting portion, a second end of the irrigation tube and a second end of the suction tube, respectively;
    wherein an outer diameter of the second tube is equal to an inner diameter of the terminal which is connected to the connecting portion, an inner diameter of the second end of the irrigation tube is equal to an outer diameter of the terminal which is connected to the second end of the irrigation tube, and an inner diameter of the second end of the suction tube is equal to an outer diameter of the terminal which is connected to second end of the suction tube;
    wherein the grip further comprises:
        a first positioning seat disposed in the accommodating space and comprising a first positioning slot; and
        a second positioning seat disposed in the accommodating space and comprising a second positioning slot;
    wherein the first positioning seat is parallel to the second positioning seat, and the first positioning seat and the second positioning seat are separated by a second distance;
    wherein the irrigation control unit further comprises:
        a first elastic member disposed in the first positioning slot of the first positioning seat for applying a first restoring force; and
        a first supporting member located in the accommodating space;
    wherein two ends of the first supporting member are connected to the first elastic member and the irrigation switch, respectively;
    wherein the first supporting member is moved in a first direction by exerting an external force provided by the irrigation switch, and the first supporting member is moved in a second direction by exerting the first restoring force of the first elastic member;
    wherein the suction control unit further comprises:
        a second elastic member disposed in the second positioning slot of the second positioning seat for applying a second restoring force; and
        a second supporting member located in the accommodating space;
    wherein two ends of the second supporting member are connected to the second elastic member and the suction switch, respectively;
    wherein the second supporting member is moved in the first direction by exerting the external force provided by the suction switch, and the second supporting member is moved in the second direction by exerting the second restoring force of the second elastic member;
    wherein the first supporting member has a first hole, the second supporting member has a second hole, the first hole is corresponding to the second hole, and the first tube is through the first hole and the second hole;
    wherein the first supporting member has a first protruding portion, the second supporting member has a second protruding portion;

wherein the first hole of the first supporting member is adjacent to the first protruding portion in a horizontal direction substantially perpendicular to the first and second directions, and the second hole of the second supporting member is adjacent to the second protruding portion in the horizontal direction.

2. The surgical irrigation and suction control apparatus of claim 1, wherein the irrigation switch and the suction switch are actuated simultaneously.

3. The surgical irrigation and suction control apparatus of claim 1, wherein the partitioning member is a Y-tube.

4. The surgical irrigation and suction control apparatus of claim 1, further comprising:
an endoscope disposed through the first tube.

5. The surgical irrigation and suction control apparatus of claim 4, wherein,
the flexible cannula further comprises a front opening;
the first tube comprises a first distal opening and a proximal opening, and the first distal opening is aligned with the front opening; and
the second tube further comprises a second distal opening, the second distal opening and the front opening are separated by a first distance, and the endoscope penetrates from the proximal opening to the first distal opening.

6. The surgical irrigation and suction control apparatus of claim 4, wherein the first tube comprises a proximal opening and an O-ring, the O-ring is disposed around the proximal opening, and the endoscope is movably connected to the O-ring.

7. The surgical irrigation and suction control apparatus of claim 1, wherein,
the first positioning seat further comprises a first supporting portion, and the second positioning seat further comprises a second supporting portion;
the irrigation tube is located between the first protruding portion and the first supporting portion, the first supporting member is pushed by the first restoring force of the first elastic member for flattening the irrigation tube by the first protruding portion of the first supporting member thereby decreasing the diameter of the irrigation tube; and
the suction tube is located between the second protruding portion and the second supporting portion, the second supporting member is pushed by the second restoring force of the second elastic member for flattening the suction tube by the second protruding portion of the second supporting member thereby decreasing the diameter of the suction tube.

8. The surgical irrigation and suction control apparatus of claim 1, further comprising:
a plug removably connected to the grip for positioning the irrigation switch or the suction switch.

9. The surgical irrigation and suction control apparatus of claim 1, wherein the first tube is flexible.

10. The surgical irrigation and suction control apparatus of claim 1, wherein the second tube is flexible.

11. The surgical irrigation and suction control apparatus of claim 1, wherein the terminal connected the second end of the irrigation tube and the terminal connected to the second end of the suction tube have a same height, and there is a height difference between the terminal connected to the connecting portion and the terminal connected to the second end of the irrigation tube.

* * * * *